United States Patent [19]

Ueda et al.

[11] Patent Number: 5,648,553
[45] Date of Patent: Jul. 15, 1997

[54] METHOD FOR PRODUCING ALDEHYDES

[75] Inventors: Akio Ueda; Masaki Nakagawa, both of Okayama, Japan

[73] Assignee: Mitsubishi Chemical Corporation, Tokyo, Japan

[21] Appl. No.: 555,073

[22] Filed: Nov. 8, 1995

[30] Foreign Application Priority Data

Dec. 9, 1994 [JP] Japan .................... 6-306218

[51] Int. Cl.$^6$ .................... C07C 45/50
[52] U.S. Cl. .................... 568/454; 568/451
[58] Field of Search .................... 568/451, 454

[56] References Cited

U.S. PATENT DOCUMENTS

| | | | |
|---|---|---|---|
| 4,247,486 | 1/1981 | Brewester et al. | 568/454 |
| 4,523,036 | 6/1985 | Cornils et al. | |
| 5,288,918 | 2/1994 | Maher et al. | 568/454 |
| 5,426,238 | 6/1995 | Mori et al. | |

OTHER PUBLICATIONS

Davy McKee, *Indications*, (The International Journal of Davy McKee), Winter 1982/83, pp. 20–28.
Kirk–Othmer; Encyclopedia of Chemical Technology;vol. 18;Fourth edition;pp. 664–666 1966.

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A method for producing aldehydes, which comprises reacting an olefin with carbon monoxide and hydrogen in a hydroformylation reaction zone in the presence of a rhodium catalyst having an organophosphorus compound as a ligand, wherein a liquid mixture derived from an effluent from the hydroformylation reaction zone, which contains an unreacted olefin and aldehyde products, is heated and then supplied to a gas-liquid contact zone, where the heated liquid mixture is countercurrently contacted with carbon monoxide and hydrogen, and a gas stream of carbon monoxide and hydrogen containing an unreacted olefin is withdrawn from the gas-liquid contact zone to separate and recover the unreacted olefin, and the recovered unreacted olefin is supplied together with the carbon monoxide and the hydrogen to the hydroformylation reaction zone.

10 Claims, 2 Drawing Sheets

METHOD FOR PRODUCING ALDEHYDES

FIELD OF THE INVENTION

The present invention relates to an improved method for hydroformylation which comprises reacting an olefin with carbon monoxide and hydrogen in a hydroformylation reaction zone in the presence of a rhodium catalyst having an organophosphorus compound as a ligand. More particularly, it relates to a method for producing aldehydes, which comprises supplying a liquid mixture derived from an effluent from the hydroformylation reaction zone, which contains an unreacted olefin and aldehyde products, to a gas-liquid contact zone, where the liquid mixture is countercurrently contacted with carbon monoxide and hydrogen to separate and recover the unreacted olefin from the liquid mixture, and supplying the recovered unreacted olefin together with the above carbon monoxide and hydrogen to the hydroformylation reaction zone.

DISCUSSION OF BACKGROUND

A method has heretofore been known wherein the hydroformylation reaction of an olefin is carried out in the presence of a rhodium catalyst. Further, several methods have been disclosed for separating an unreacted olefin, aldehyde products and the catalyst from the reaction solution of hydroformylation reaction products.

For example, Japanese Unexamined Patent Publication No. 70634/1984 discloses a method for producing aldehydes which comprises reacting an olefin with carbon monoxide and hydrogen in the presence of a water-soluble rhodium-phosphine complex compound, and it discloses, as a method for recovering the unreacted olefin, a method of using a stripping tower by means of a synthesis gas (a mixture of carbon monoxide and hydrogen).

Further, INDICATIONS, Winter 1982/83 (The International Journal of Davy Mackee) discloses a method for producing butyraldehyde by reacting propylene with carbon monoxide and hydrogen in the presence of a rhodium catalyst having triphenylphosphine (TPP) as a ligand, and it discloses a process wherein by a gas stripping type reaction system, unreacted propylene, hydrogen, carbon monoxide and butyraldehyde are withdrawn as a gaseous effluent and condensed to obtain a liquid product of butyraldehyde containing propylene, which is directly charged into a stripping tower and contacted with carbon monoxide and hydrogen to separate and recover the unreacted olefin from the liquid product, and the recovered unreacted olefin is supplied together with the carbon monoxide and the hydrogen to the hydroformylation reactor. In this case, butyraldehyde discharged from the stripping tower is further subjected to a subsequent step of distillation for recovery of the dissolved gas.

Further, Japanese Patent Application No. 138630/1993 discloses a hydroformylation method of an olefin, which comprises reacting an olefin with carbon monoxide and hydrogen in a hydroformylation reaction zone in the presence of a rhodium catalyst having a trivalent organophosphorus compound as a ligand, wherein a liquid mixture derived from an effluent from the hydroformylation reaction zone, which contains an unreacted olefin, aldehyde products and the catalyst, is contacted with carbon monoxide and hydrogen to separate and recover the unreacted olefin from the reaction solution without substantially deactivating the rhodium catalyst, and the recovered unreacted olefin is supplied together with the carbon monoxide and the hydrogen to the hydroformylation reaction zone.

Thus, many proposals have been made for a method of countercurrently contacting a gas mixture of carbon monoxide and hydrogen to be supplied to the hydroformylation reaction with the product stream in a gas-liquid contact zone, when an unreacted olefin is to be recovered from the product stream in the hydroformylation process of an olefin.

An unrecovered dissolved olefin in the above gas-liquid contact zone will be lost or will have to be recovered by a further recovery means such as fractional distillation. Accordingly, the degassing efficiency in the gas-liquid contact zone has been substantially influential over the economy of the process.

In every one of the above methods, the amounts of carbon monoxide and hydrogen as the gas for recovery of the unreacted olefin must be controlled to meet the mass balance in the hydroformylation reactor, and the degree of freeness for a change of the amounts is limited. Accordingly, if the amount of a dissolved olefin contained in the product stream increases, the degassing efficiency deteriorates, and from the viewpoint of economy, there is naturally the upper limit for the olefin concentration in the hydroformylation reactor. On the other hand, from the viewpoint of the reaction efficiency, the olefin concentration in the hydroformylation reactor should better be high to attain a high reaction rate and high productivity.

Accordingly, it has been difficult by the conventional technology to increase the olefin concentration in the hydroformylation reactor without increasing the amount of an unrecovered olefin in the gas-liquid contact zone in the hydroformylation process of an olefin which comprises recovering an unreacted olefin from the product stream by countercurrently contacting the hydroformylation reaction products with a gas mixture of carbon monoxide and hydrogen to be supplied to the hydroformylation reaction in a gas-liquid contact tower.

SUMMARY OF THE INVENTION

It is an object of the present invention to provide an industrially advantageous method for producing aldehydes, whereby the olefin recovery efficiency in the gas-liquid contact zone can be increased and the olefin concentration in the hydroformylation reactor can be made high.

The present inventors have conducted extensive studies on the above problems and as a result, have found it possible to solve the above problems by heating the liquid mixture of hydroformylation reaction products, when the hydroformylation reaction products are countercurrently intimately contacted with carbon monoxide and hydrogen to be supplied to the hydroformylation reaction zone. The present invention has been accomplished on the basis of this discovery.

Thus, the present invention provides a method for producing aldehydes, which comprises reacting an olefin with carbon monoxide and hydrogen in a hydroformylation reaction zone in the presence of a rhodium catalyst having an organophosphorus compound as a ligand, wherein a liquid mixture derived from an effluent from the hydroformylation reaction zone, which contains an unreacted olefin and aldehyde products and contains substantially no rhodium catalyst, is heated and then supplied to a gas-liquid contact zone, where the heated liquid mixture is countercurrently contacted with carbon monoxide and hydrogen, and a gas stream of carbon monoxide and hydrogen containing an unreacted olefin is withdrawn from the gas-liquid contact zone to separate and recover the unreacted olefin, and the recovered unreacted olefin is supplied together with the carbon monoxide and the hydrogen to the hydroformylation reaction zone.

The present invention also provides a method for producing aldehydes, which comprises reacting an olefin with carbon monoxide and hydrogen in a hydroformylation reaction zone in the presence of a rhodium catalyst having an organophosphorus compound as a ligand, wherein a liquid mixture derived from an effluent from the hydroformylation reaction zone, which contains an unreacted olefin and aldehyde products, and substantially contains the rhodium catalyst, is heated and then supplied to a gas-liquid contact zone, where the heated liquid mixture is countercurrently contacted with carbon monoxide and hydrogen, and a gas stream of carbon monoxide and hydrogen containing an unreacted olefin is withdrawn from the gas-liquid contact zone, to separate and recover the unreacted olefin, and then the gas stream is partially condensed by a condenser, and an uncondensed gas containing an unreacted olefin is supplied together with the carbon monoxide and the hydrogen to the hydroformylation reaction zone, and the condensed liquid is refluxed to the gas-liquid contact zone.

DETAILED DESCRIPTION OF THE PREFERRED EMBODIMENTS

Figure 1:
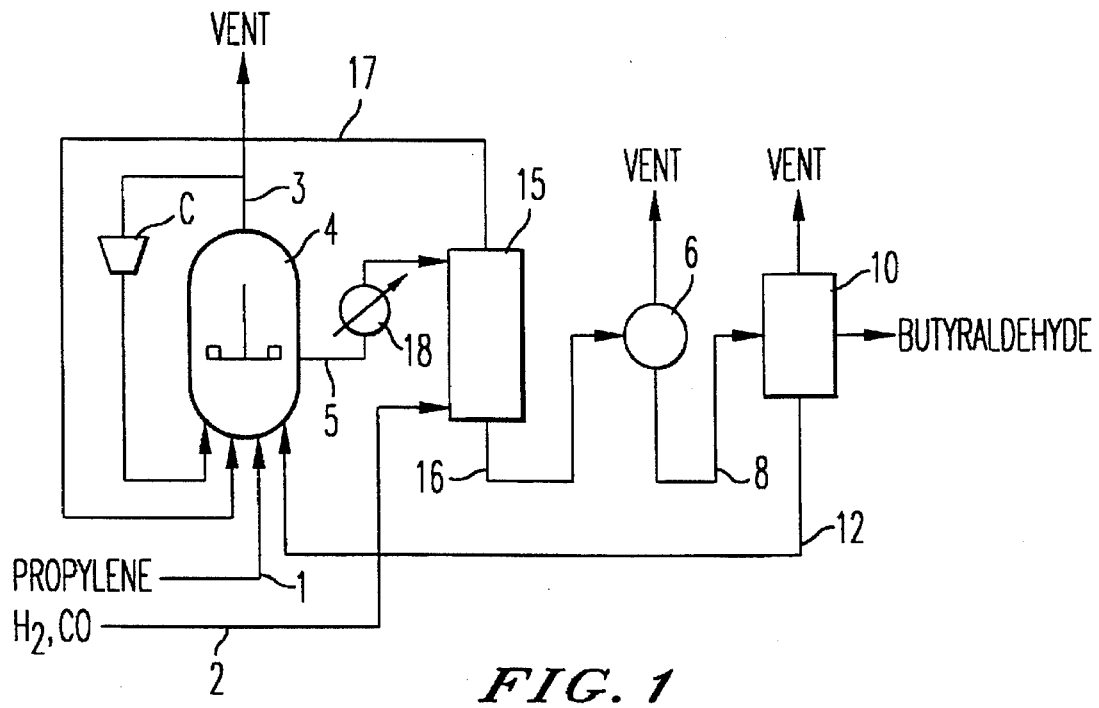
FIG. 1 is a flow chart of the process used in Examples 1 to 3 and Comparative Examples 1 and 2.

Now, the present invention will be described in detail.

With respect to the olefin to be used in the present invention, there is no critical limitation, and a single olefin or an olefin mixture may be employed. However, preferred olefins are olefins having from 2 to 5 carbon atoms or their mixtures. The most preferred olefin is propylene. Further, a starting material having low olefin purity such as the one containing hydrocarbons other than olefin, such as paraffins, may also be suitably employed.

The starting material olefin may be used usually without any special pretreatment. However, it is possible to employ the one having a sulfur content or halogen content known as a catalyst poison, or dienes and trienes, or peroxides, removed by conventional methods such as adsorption, extraction, distillation, heat treatment or separation by means of membranes.

As the catalyst, a rhodium catalyst having an organophosphorus compound as a ligand is employed. The organic phosphorus compound may, for example, be a trialkylphosphine such as tributylphosphine or trioctylphosphine, a triarylphosphine such as triphenylphosphine, tritolylphosphine, or a triarylphosphine having hydrogen of a phenyl group substituted by a sulfonic group or halogen, a tricycloalkylphosphine such as tricyclohexylphosphine, an alkylarylphosphine such as monobutyldiphenylphosphine or dipropylphenylphosphine, a cycloalkylarylphosphine, or an alkylcycloalkylphosphine. Further, a trialkyl phosphite, a triaryl phosphite such as triphenyl phosphite or trinaphthyl phosphite which may have a substituent, or an alkylaryl phosphite, may also be employed. Specifically, compounds disclosed in U.S. Pat. Nos. 3,415,906, 4,599,206, 4,351,759, 4,748,261, 4,567,306, 5,235,113 and 5,227,532 may be mentioned. However, the present invention is by no means restricted by the type of the organophosphorus compound.

Two or more members among these organophosphorus compounds may be employed as mixed ligands. Further, the above organophosphorus compound may be used in combination with a pentavalent organophosphorus compound such as triphenylphosphine oxide.

As the rhodium source, an organic salt such as rhodium acetyl acetonate or rhodium acetate, an inorganic salt such as rhodium nitrate or an oxide such as rhodium oxide may also be used other than a rhodium complex such as hydride carbonyltris(triphenylphosphine)rhodium or acetoxy bis(triphenylphosphine)rhodium. Rhodium may directly be supplied to the hydroformylation reactor. However, it is also possible that rhodium is treated together with a ligand of an organophosphorus compound with carbon monoxide and hydrogen under an elevated temperature and pressure in a solvent outside the reactor to preliminarily prepare a catalyst solution. The solvent for the preparation of this catalyst is usually selected from the solvents for reaction which will be described hereinafter. However, such a solvent may not necessarily be the same as the solvent for reaction. With respect to the conditions for preparation of the catalyst, the rhodium concentration is usually from a few ppm to a few wt %, the molar ratio of the ligand of the organophosphorus compound to rhodium is usually P/Rh=1 to 10,000, the temperature is from 60° to 200° C., the pressure is from atmospheric pressure to 200 kg/cm$^2$G, and the treating time is within a range of from a few minutes to some dozen hours.

The above treatment may be carried out in a batch system or a continuous system.

As the solvent for the hydroformylation reaction, the olefin itself may be used, or the resulting aldehyde or high boiling point substances produced as by-products may be used as the solvent. Further, a solvent which is capable of dissolving the catalyst and which presents no adverse effects to the reaction, for example, an aliphatic hydrocarbon such as hexane or octane, an aromatic hydrocarbon such as toluene or xylene, an alicyclic hydrocarbon such as cyclohexane, an alcohol such as butanol, octanol, polyethylene glycol or polypropylene glycol, an ether such as trigrime or tetragrime, an ester such as dioctyl phthalate, or water, may also be used. With respect to the hydroformylation reaction conditions, the hydrogen partial pressure is usually from 0.1 to 200 kg/cm$^2$G, the carbon monoxide partial pressure is from 0.1 to 200 kg/cm$^2$G, the total pressure is from a few kg/cm$^2$G to 300 kg/cm$^2$G, the ratio of hydrogen partial pressure/carbon monoxide partial pressure=0.1 to 10, the temperature is from 60° to 200° C., the rhodium concentration is from a few wt ppm to a few wt %, P (in the organophosphorus compound ligand)/Rh=1 to 10,000 (molar ratio), and the reaction time is from a few minutes to some dozen hours.

As a method for obtaining aldehyde products from the reaction zone of hydroformylation conducted as described above, there may be mentioned a method wherein a rhodium catalyst is substantially incorporated to the feed solution to a gas-liquid contact tower, or a method wherein substantially no rhodium catalyst is incorporated.

According to the present invention, the separation efficiency of the unreacted olefin can be improved by heating a liquid mixture of reaction products supplied to the gas-liquid contact tower commonly employed in these methods, to a proper temperature.

As a method for substantially incorporating the rhodium catalyst to the feed solution to the gas-liquid contact tower, a method may, for example, be mentioned in which a reaction solution withdrawn from the hydroformylation reaction zone, which contains an unreacted olefin, aldehyde products and the catalyst, is introduced into the upper part for the gas-liquid contact tower without pressure release i.e. under substantially the same pressure as in the reaction zone, while carbon monoxide and hydrogen are introduced from the tower bottom and countercurrently contacted with the above reaction solution withdrawn from the reaction zone, whereby the unreacted olefin obtained from the tower top is recycled together with the carbon monoxide and hydrogen to the hydroformylation reaction zone.

In this method, it is preferred to heat the liquid mixture of reaction products supplied to the gas-liquid contact tower to a temperature higher than the reaction temperature in the hydroformylation reaction zone, preferably to a temperature of not higher than 200° C., more preferably to a temperature higher by at least 5° C. than the reaction temperature and not higher than 190° C., whereby the separation efficiency of the unreacted olefin can be improved.

The reaction solution having the unreacted olefin removed in the gas-liquid contact tower, is separated by a separating means such as distillation into the formed aldehydes and the catalyst solution, and the catalyst solution is recycled to the hydroformylation reaction zone.

On the other hand, as a first method in which substantially no rhodium catalyst is incorporated in the feed solution to the gas-liquid contact tower, a method may, for example, be mentioned in which the reaction solution withdrawn from the hydroformylation reaction zone, which contains an unreacted olefin, aldehyde products and the catalyst, is subjected to flashing or simple distillation in a single stage or a plurality of stages to separate it into aldehyde products containing the unreacted olefin and the catalyst solution, the catalyst solution is recycled to the hydroformylation reaction zone, while the aldehyde products containing the unreacted olefin are charged into a gas-liquid contact tower and countercurrently contacted with carbon monoxide and hydrogen, whereupon the unreacted olefin is recycled together with the carbon monoxide and hydrogen to the hydroformylation reaction zone. In this method, it is preferred to heat the aldehyde products containing the unreacted olefin supplied to the gas-liquid contact tower to a temperature higher than the condensation temperature of the aldehydes and not higher than 120° C., whereby the separation efficiency of the unreacted olefin can be improved.

As a second method, a method may, for example, be mentioned which is applicable in a case where water is used for the hydroformylation reaction, and the reaction is carried out by a water-soluble catalyst, and wherein a reaction solution withdrawn from the hydroformylation reaction zone, which contains an unreacted olefin, aldehyde products and the catalyst, or a mixed solution obtained by adding water to such a reaction solution, is subjected to liquid separation by a liquid separation tank into an organic phase containing the unreacted olefin and the aldehyde products and an aqueous phase containing the catalyst, whereupon the aqueous phase is recycled to the hydroformylation reaction zone, while the organic phase containing the unreacted olefin and the aldehyde products is led to a gas-liquid contact tower in the same manner as in the first method to recover the unreacted olefin. In this method, it is preferred to heat the organic phase supplied to the gas-liquid contact tower to a temperature higher than the temperature for liquid separation into the aqueous phase and the organic phase (the liquid separation temperature) and not higher than 120° C., more preferably to a temperature higher by at least 5° C. than the liquid separation temperature and not higher than 120° C., whereby the separation efficiency of the unreacted olefin can be improved.

Further, as a third method, a method may, for example, be mentioned wherein unreacted carbon monoxide, hydrogen, olefin and aldehyde products are withdrawn as a gas stream from the hydroformylation reaction zone and introduced into a condenser, whereby aldehyde products containing the unreacted olefin are obtained in the form of a liquid, while a non-condensed gas is recycled to the hydroformylation reaction zone, and the aldehyde products containing the unreacted olefin are led to a gas-liquid contact tower in the same manner as in the first and second methods to recover the unreacted olefin. In this method, it is preferred to heat the liquid mixture after condensation which is supplied to the gas-liquid contact tower to a temperature higher by at least 5° C. than the condensation temperature of the aldehydes and not higher than 100° C., whereby the the separation efficiency of the unreacted olefin can be improved.

The above mentioned first to third methods are different only in the means for separating the catalyst and the aldehyde products, and they are the same in that the feed solution to the gas-liquid contact tower contains no rhodium catalyst.

As the heat source for heating, steam or exhaust gas from other steps in the plant may be employed.

In the present invention, in order to avoid inclusion of formed aldehydes in a substantial amount in the tower top gas (pipeline 17 in FIG. 1, pipeline 11 in FIG. 2) from the gas-liquid contact zone, which tend to increase an undesirable polycondensation product of aldehydes in the reactor (4), it is preferred to partially condense the gas stream from the gas-liquid contact zone by a condenser, and to reflux the condensed liquid to the gas-liquid contact zone. Here, the gas temperature at the outlet of the condenser is preferably within a range from a temperature at which the olefin would not condense (such as at least 0° C.) to a temperature lower by at least 10° C. than the gas temperature at the top of the gas-liquid contact tower.

It has been common to employ a method of increasing the amount of the liquid in the reactor in order to avoid an increase of high boiling by-product in the reactor, e.g. a method of increasing the amount of the recycling liquid in a liquid recycling system (e.g. by increasing the flow rates in pipelines 5, 16, 8 and 12 in FIG. 1, as described hereinafter), or a method of increasing the amount of a recycling gas in a gas recycling system (e.g. by increasing the load of the recycling compressor C in FIG. 2, as described hereinafter). However, these methods have had a problem that they bring about a substantial increase in the consumption of the driving power source. However, by adopting the above-mentioned method of recycling the gas stream from the gas-liquid contact zone, it is possible to suppress the increase in the power consumption and to minimize inclusion of aldehydes in the tower top gas.

According to the present invention, it is possible to increase the olefin concentration in the hydroformylation reaction zone without increasing a loss of the olefin, by increasing the separation efficiency of the unreacted olefin in the gas-liquid contact zone, and consequently, it is possible to increase the rate of the hydroformylation reaction.

Now, specific embodiments of the present invention will be described in further detail with reference to Examples. However, it should be understood that the present invention is by no means restricted by such specific Examples.

EXAMPLES 1 TO 3 AND COMPARATIVE EXAMPLES 1 AND 2

Using an apparatus as shown in FIG. 1, the hydroformylation reaction of propylene (hereinafter referred to as PPY)

was carried out. With respect to the conditions of the catalyst solution in the reactor (4), Rh was 233 mg/l, and triphenylphosphine (hereinafter referred to as TPP) was 0.573 mol/l. The reactor (4) was maintained at 100° C. under a total pressure of 15.5 kg/cm$^2$G, and propylene (pipeline 1) was charged at a rate of 7.5 kg/hr. The propylene (pipeline 1) used was the one having a purity of 99 mol %, and water gas (pipeline 2) used was a gas having a H$_2$/CO ratio of 1.015. They were supplied to maintain the pressure of the reactor (4) at a level of 15.5. kg/cm$^2$G. Inert gas and a part of unreacted material were discharged from a vent (3). A heat exchanger (18) was provided to adjust the temperature of the feed to the gas-liquid contact tower. As the gas-liquid contact tower (15), a packed tower corresponding to a theoretical plate number of 12 plates, was employed. Adjustment of the PPY concentration in the reactor (4) was carried out by controlling the liquid level of the reactor (4) and the amount of the discharge to the vent (3). The conditions for the hydroformylation reactor and the gas-liquid contact tower, and the results are shown in Table 1.

EXAMPLES 4 AND 5 AND COMPARATIVE EXAMPLES 3 AND 4

Figure 2:
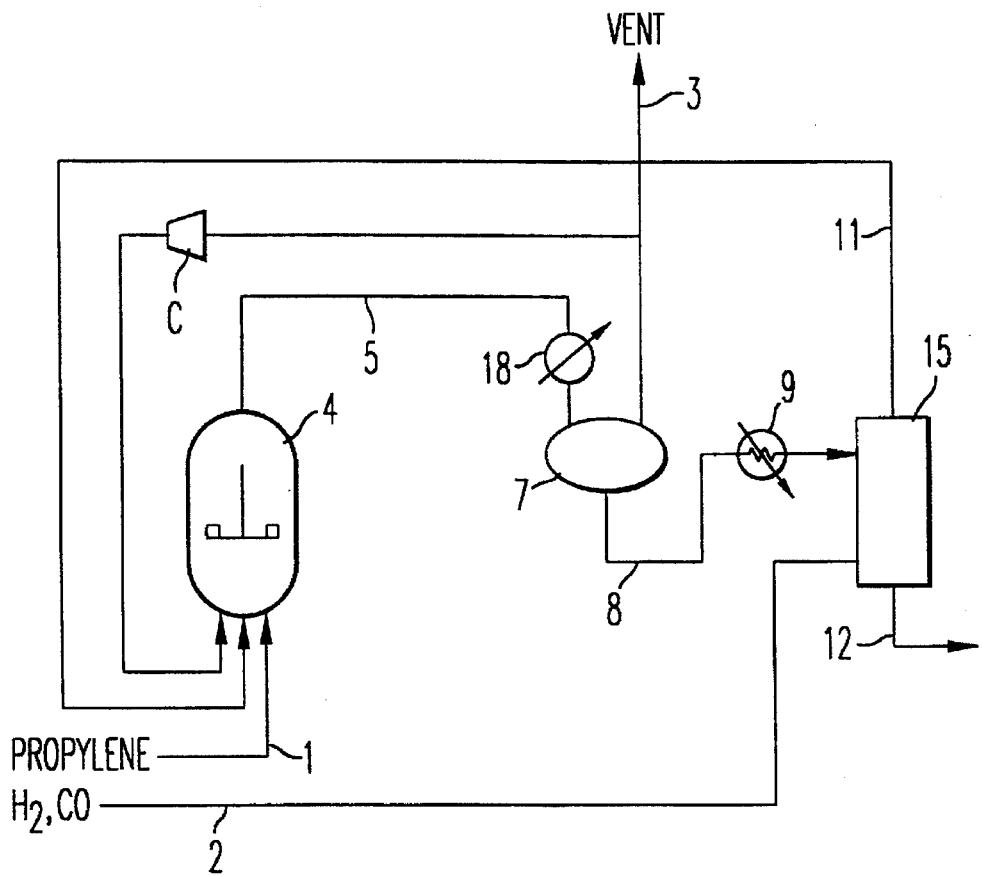
FIG. 2 is a flow chart of the process used in Examples 4 and 5 and Comparative Examples 3 and 4.

Using an apparatus as shown in FIG. 2, a hydroformylation reaction of PPY was carried out. With respect to the conditions of the catalyst in the reactor (4), Rh was 233 mg/l, and TPP was 0.573 mol/l. The reactor (4) was maintained at 90° C. under a total pressure of 17 kg/cm$^2$G, and propylene (pipeline 1) was charged at a rate of 7.5 kg/hr. The propylene (pipeline 1) used was the one having a purity of 99.9 mol %, and water gas (pipeline 2) used was a gas having a H$_2$/CO ratio of 1.02. They were supplied to maintain the pressure of the reactor (4) to a level of 17 kg/cm$^2$G. Inert gas and a part of unreacted material were discharged from a vent (3). The reaction products withdrawn from the hydroformylation reaction zone in the form of a gas stream, were condensed by passing cooling water to a heat exchanger (18), and the amount of the cooling water was adjusted so that the temperature of a liquid receiving tank (7) became 40° C. A heat exchanger (9) was provided to adjust the feeding temperature of the aldehyde product stream (8) to a gas-

TABLE 1

|  |  | Comparative Example 1 | Comparative Example 2 | Example 1 | Example 2 | Example 3 |
| --- | --- | --- | --- | --- | --- | --- |
| Reactor |  |  |  |  |  |  |
| Amount of propylene charged | Kg/hr | 7.4 | 7.4 | 7.4 | 7.4 | 7.4 |
| Concentration of propylene in liquid | mol/l | 0.94 | 1.24 | 0.97 | 1.03 | 1.83 |
| Reaction rate | mol/l/hr | 2.9 | 3.7 | 3.0 | 3.1 | 5.2 |
| Yield of high boiling by-product*$^1$ | % | 0.51 | 0.39 | 0.57 | 0.66 | 0.46 |
| Contercurrent contact tower |  |  |  |  |  |  |
| Amount of feed solution | Kg/hr | 60.7 | 61.4 | 64.2 | 73.7 | 118.6 |
| Feed temperature | °C. | 100 | 100 | 130 | 165 | 190 |
| Propylene concentration in feed solution | mol/l | 0.94 | 1.24 | 0.97 | 10.3 | 1.83 |
| Propylene concentration in bottoms | mol/l | $4.8 \times 10^{-3}$ | $5.9 \times 10^{-3}$ | $2.9 \times 10^{-3}$ | $2.3 \times 10^{-3}$ | $2.3 \times 10^{-3}$ |
| Recovery ratio of propylene | % | 99.6 | 99.6 | 99.8 | 99.9 | 99.9 |
| Loss ratio of propylene*$^2$ | % | 0.16 | 0.20 | 0.10 | 0.08 | 0.08 |
| Tower top condenser |  | Nil | Nil | Nil | Nil | Nil |

*$^1$Yield of high boiling by-product = $\dfrac{\text{Amount of propylene converted to high boiling by-product}}{\text{Amount of propylene charged to the reactor}} \times 100$

*$^2$Loss ratio of propyelene = $\dfrac{\text{Amount of propylene in bottoms of the countercurrent contact tower}}{\text{Amount of propylene charged to the reactor}} \times 100$ In Comparative Examples 1 and 2, no heating was carried out by a heat exchanger (18), and only the PPY concentration in the reactor (4) was changed, whereby it was observed that the loss ratio of PPY tended to increase with an increase of this PPY concentration. On the other hand, in Examples 1 to 3, heating was carried out by the heat exchanger (18) to 130° C., 165° C. and 190° C., respectively. Even when the PPY concentration in the reactor (4) increased by heating, the loss ratio of PPY did not increase, and on the contrary, the loss ratio of PPY tended to decrease. Further, it is evident that the reaction rate increased substantially with the increase of the PPY concentration.

liquid contact tower (15). As the gas-liquid contact tower (15), a packed tower corresponding to a theoretical plate number of 14 plates, was employed. Adjustment of the PPY concentration in the reactor (4) was carried out by controlling the amount of the liquid in the reactor (4) and the amount of discharge to the vent (3). The conditions for the hydroformylation reactor and the gas-liquid contact tower, and the results are shown in Table 2.

TABLE 2

|  |  | Comparative Example 3 | Comparative Example 4 | Example 4 | Example 5 |
|---|---|---|---|---|---|
| Reactor | | | | | |
| Amount of propylene charged | Kg/hr | 7.5 | 7.5 | 7.5 | 7.5 |
| Concentration of propylene in liquid | mol/l | 0.64 | 0.83 | 1.06 | 1.42 |
| Reaction rate | mol/l/hr | 1.4 | 1.7 | 2.0 | 2.6 |
| Yield of high boiling by-product*[1] | % | 1.82 | 1.34 | 1.14 | 0.82 |
| Contercurrent contact tower | | | | | |
| Amount of feed solution | Kg/hr | 12.9 | 13.3 | 15.6 | 23.1 |
| Feed temperature | °C. | 40 | 40 | 70 | 90 |
| Propylene concentration in feed solution | mol/l | 2.14 | 2.83 | 3.55 | 4.54 |
| Propylene concentration in bottoms | mol/l | $1.1 \times 10^{-1}$ | $2.7 \times 10^{-1}$ | $1.1 \times 10^{-1}$ | $1.6 \times 10^{-2}$ |
| Recovery ratio of propylene | % | 96.3 | 93.0 | 98.2 | 99.9 |
| Loss ratio of propylene*[2] | % | 1.03 | 2.64 | 1.06 | 0.15 |
| Tower top condenser | | Nil | Nil | Nil | Nil |

*[1] Yield of high boiling by-product = $\dfrac{\text{Amount of propylene converted to high boiling by-product}}{\text{Amount of propylene charged to the reactor}} \times 100$

*[2] Loss ratio of propyelene = $\dfrac{\text{Amount of propylene in bottoms of the countercurrent contact tower}}{\text{Amount of propylene charged to the reactor}} \times 100$ In Comparative Examples 3 and 4, no heating was carried out by a heat exchanger (9), and only the PPY concentration in the reactor (4) was changed, whereby it was observed that the loss ratio of PPY tended to increase with an increase of this PPY concentration. On the other hand, in Examples 4 and 5, heating was carried out by the heat exchanger (9) to 70° C. and 90° C., respectively. It is evident that even when the PPY concentration in the reactor (4) increased by heating, the loss ratio of PPY did not increase. Further, it is evident that the reaction ratio distinctly increased with an increase of the PPY concentration.

EXAMPLES 6 AND 7

Figure 3:
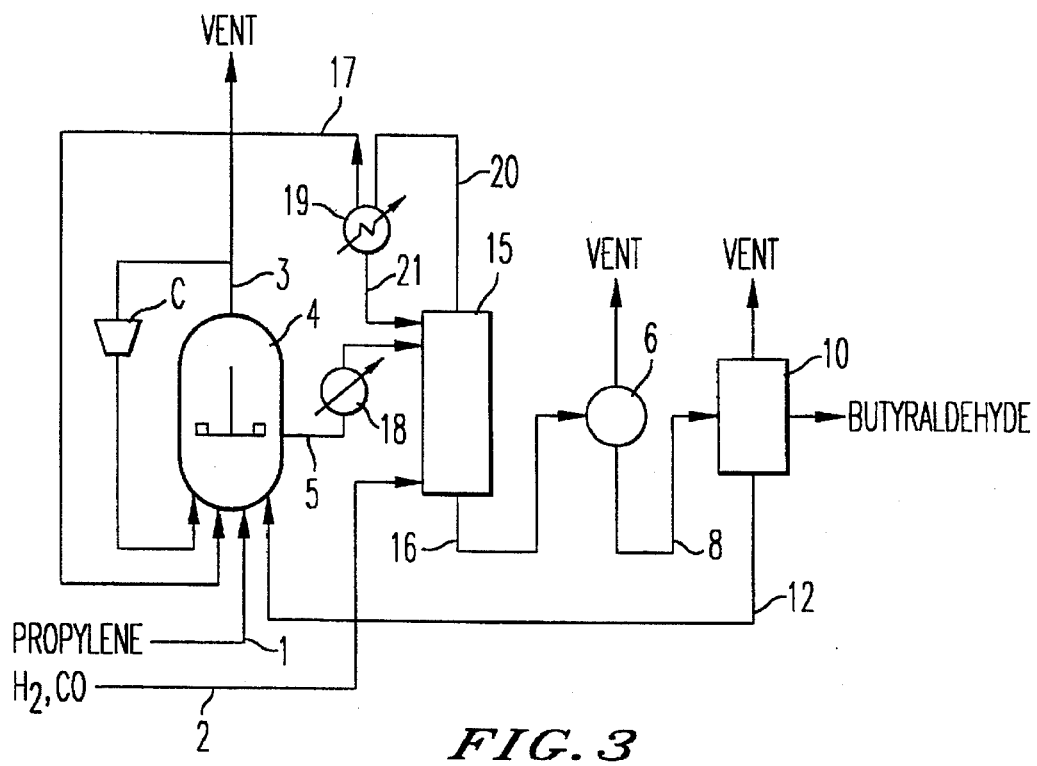
FIG. 3 is a flow chart of the process used in Examples 6 and 7.

A reaction was carried out in accordance with the flow chart as shown in FIG. 3 wherein in the liquid recycling process as shown in FIG. 1, a condenser (19) is provided in the tower top gas line of the gas-liquid contact tower (15), so that the condensed liquid is refluxed to the top of the gas-liquid contact tower (15) by a pipeline (21). Cooling water was passed through the condenser (19) to cool the tower top gas to 40° C. The conditions for the hydroformylation reactor and the gas-liquid contact tower, and the results are shown in Table 3.

EXAMPLE 8

Figure 4:
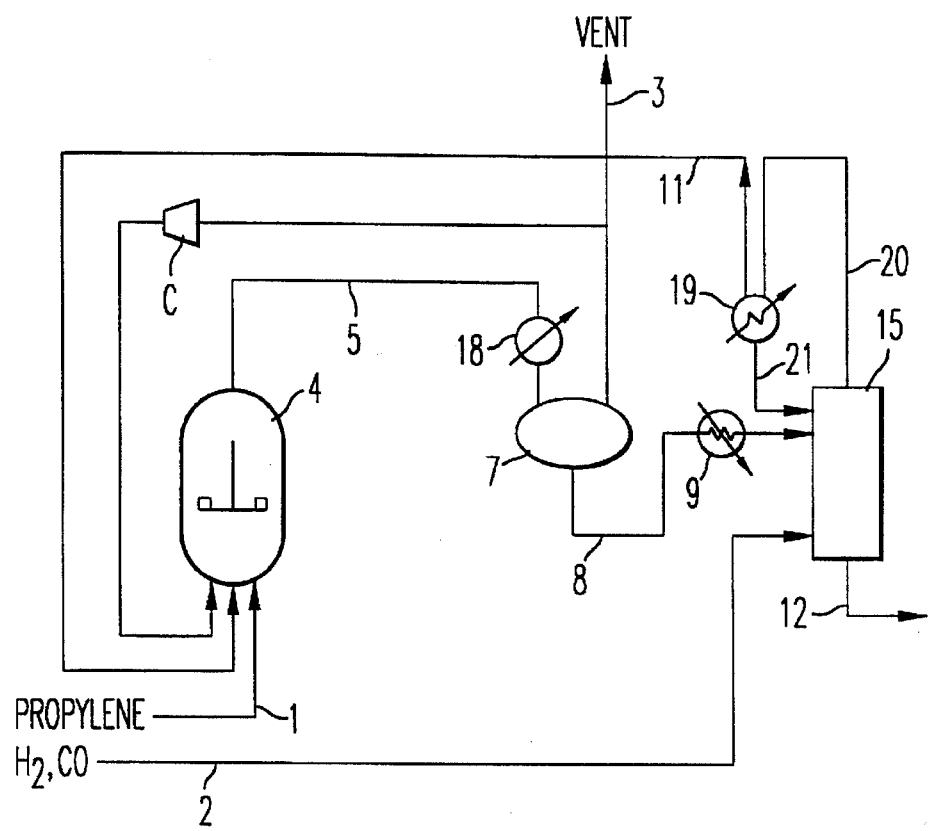
FIG. 4 is a flow chart of the process used in Example 8.

A reaction was carried out in accordance with the flow chart as shown in FIG. 4, wherein in the gas recycling process shown in FIG. 2, a condenser (19) was provided in the tower top gas line of the gas-liquid contact tower (15), so that the condensed liquid is refluxed to the top of the gas-liquid contact tower (15) by a pipeline (21). Cooling water was passed through the condenser (19) to cool the tower top gas to 40° C. The conditions for the hydroformylation reactor and the gas-liquid contact tower, and the results are shown in Table 3.

TABLE 3

|  |  | Example 6 | Example 7 | Example 8 |
|---|---|---|---|---|
| Reactor | | | | |
| Amount of propylene charged | Kg/hr | 7.4 | 7.4 | 7.5 |
| Concentration of propylene in liquid | mol/l | 0.92 | 0.98 | 1.05 |
| Reaction rate | mol/l/hr | 2.9 | 3.0 | 2.2 |
| Yield of high boiling by-product*[1] | % | 0.47 | 0.46 | 1.00 |
| Contercurrent contact tower | | | | |
| Amount of feed solution | Kg/hr | 58.7 | 59.0 | 15.6 |
| Feed temperature | °C. | 100 | 165 | 70 |
| Propylene concentration in | mol/l | 0.92 | 0.98 | 3.53 |

TABLE 3-continued

|  |  | Example 6 | Example 7 | Example 8 |
|---|---|---|---|---|
| feed solution |  |  |  |  |
| Propylene concentration in bottoms | mol/l | $5.1 \times 10^{-3}$ | $2.5 \times 10^{-3}$ | $1.1 \times 10^{-1}$ |
| Recovery ratio of propylene | % | 99.6 | 99.8 | 98.1 |
| Loss ratio of propylene*[2] | % | 0.17 | 0.09 | 1.10 |
| Tower top condenser |  | Present | Present | Present |

*[1]Yield of high boiling by-product = $\dfrac{\text{Amount of propylene converted to high boiling by-product}}{\text{Amount of propylene charged to the reactor}} \times 100$

*[2]Loss ratio of propyelene = $\dfrac{\text{Amount of propylene in bottoms of the countercurrent contact tower}}{\text{Amount of propylene charged to the reactor}} \times 100$ With respect to the liquid recycling system, from the comparison between Example 6 and Comparative Example 1 and between Example 7 and Example 2, it is evident that even when the temperature of the feed to the countercurrent contact tower is the same, the high boiling conversion is reduced by employing a tower top condenser for the countercurrent contact tower.

Likewise, also with respect to the gas circulation system, from the comparison between Example 4 and Example 8, it is evident that the high boiling conversion is reduced by employing a tower top condenser for the countercurrent contact tower.

By producing aldehydes by the method of the present invention, it is possible to increase the separation efficiency of an unreacted olefin in the gas-liquid contact zone. Namely, it is possible to increase the olefin concentration in the hydroformylation reaction zone without increasing the loss of the olefin. Consequently, it is possible to increase the rate of the hydroformylation reaction. Thus, the method of the present invention is highly advantageous in an industrial application.

What is claimed is:

1. A method for producing aldehydes, which comprises reacting an olefin with carbon monoxide and hydrogen in a hydroformylation reaction zone in the presence of a rhodium catalyst having an organophosphorus compound as a ligand, wherein a liquid mixture derived from an effluent from the hydroformylation reaction zone, which contains an unreacted olefin and aldehyde products and contains substantially no rhodium catalyst, is heated and then supplied to a gas-liquid contact zone, where the heated liquid mixture is countercurrently contacted with carbon monoxide and hydrogen, and a gas stream of carbon monoxide and hydrogen containing an unreacted olefin is withdrawn from the gas-liquid contact zone to separate and recover the unreacted olefin, and the recovered unreacted olefin is supplied together with the carbon monoxide and the hydrogen to the hydroformylation reaction zone.

2. The method for producing aldehydes according to claim 1, wherein the liquid mixture is aldehyde products containing the unreacted olefin, which is obtained by flashing or simple distillation of a reaction solution containing the unreacted olefin, the aldehyde products and the catalyst withdrawn from the hydroformylation reaction zone.

3. The method for producing aldehydes according to claim 1, wherein the liquid mixture is an organic phase containing the unreacted olefin and the aldehyde products, which is obtained by oil-water separation of a reaction solution withdrawn from the hydroformylation reaction zone employing a water-soluble catalyst, or of a mixed solution obtained by adding water to such a reaction solution.

4. The method for producing aldehydes according to claim 1, wherein the liquid mixture is obtained by withdrawing the unreacted olefin and the aldehyde products in a gas stream from the hydroformylation reaction zone, followed by condensation.

5. The method for producing aldehydes according to claim 1, wherein a gas stream from the gas-liquid contact zone is partially condensed by a condenser, and the condensed liquid is refluxed to the gas-liquid contact zone.

6. The method for producing aldehydes according to claim 1, wherein the olefin is propylene, and the aldehyde products are n-butyraldehyde and isobutyraldehyde.

7. A method for producing aldehydes, which comprises reacting an olefin with carbon monoxide and hydrogen in a hydroformylation reaction zone in the presence of a rhodium catalyst having an organophosphorus compound as a ligand, wherein a liquid mixture derived from an effluent from the hydroformylation reaction zone, which contains an unreacted olefin and aldehyde products, and substantially contains the rhodium catalyst, is heated and then supplied to a gas-liquid contact zone, where the heated liquid mixture is countercurrently contacted with carbon monoxide and hydrogen, and a gas stream of carbon monoxide and hydrogen containing an unreacted olefin is withdrawn from the gas-liquid contact zone, to separate and recover the unreacted olefin, and then the gas stream is partially condensed by a condenser, and an uncondensed gas containing an unreacted olefin is supplied together with the carbon monoxide and the hydrogen to the hydroformylation reaction zone, and the condensed liquid is refluxed to the gas-liquid contact zone.

8. The method for producing aldehydes according to claim 7, wherein the liquid mixture is heated to a temperature higher than the reaction temperature in the hydroformylation reaction zone and then supplied to the gas-liquid contact zone.

9. The method for producing aldehydes according to claim 7, wherein the liquid mixture is heated to a temperature of not higher than 200° C. and then supplied to the gas-liquid contact zone.

10. The method for producing aldehydes according to claim 7, wherein the olefin is propylene, and the aldehyde products are n-butyraldehyde and isobutyraldehyde.

* * * * *